(12) United States Patent
Chatenet

(10) Patent No.: US 10,101,300 B2
(45) Date of Patent: Oct. 16, 2018

(54) DEVICE FOR INSPECTING A SURFACE OF AN ELECTRICALLY CONDUCTIVE PART

(71) Applicant: Safran Aircraft Engines, Paris (FR)

(72) Inventor: Luc Henri Chatenet, Moissy-Cramayel (FR)

(73) Assignee: Safran Aircraft Engines, Paris (FR)

( * ) Notice: Subject to any disclaimer, the term of this patent is extended or adjusted under 35 U.S.C. 154(b) by 0 days.

(21) Appl. No.: 14/903,155

(22) PCT Filed: Jun. 26, 2014

(86) PCT No.: PCT/FR2014/051618
§ 371 (c)(1),
(2) Date: Jan. 6, 2016

(87) PCT Pub. No.: WO2015/004364
PCT Pub. Date: Jan. 15, 2015

(65) Prior Publication Data
US 2016/0161449 A1    Jun. 9, 2016

(30) Foreign Application Priority Data

Jul. 10, 2013  (FR) ...................................... 13 56779

(51) Int. Cl.
*G01N 27/90*        (2006.01)

(52) U.S. Cl.
CPC ........... *G01N 27/90* (2013.01); *G01N 27/902* (2013.01); *G01N 27/904* (2013.01); *G01N 27/9033* (2013.01)

(58) Field of Classification Search
CPC .... G01N 27/87; G01N 27/9013; G01N 27/90; G01N 27/9033; G01N 27/902;
(Continued)

(56) References Cited

U.S. PATENT DOCUMENTS

| 4,303,884 A | * | 12/1981 | Malick | ................. G01N 27/904 |
| | | | | 324/220 |
| 4,372,161 A | * | 2/1983 | de Buda | ................. F16L 55/34 |
| | | | | 15/104.16 |

(Continued)

FOREIGN PATENT DOCUMENTS

| EP | 1 245 953 A1 | 10/2002 |
| JP | 4-264256 | 9/1992 |

(Continued)

OTHER PUBLICATIONS

International Search Report dated Oct. 6, 2014, in PCTFR2014/051618 filed Jun. 26, 2014.

*Primary Examiner* — Son Le
*Assistant Examiner* — Dustin Dickinson
(74) *Attorney, Agent, or Firm* — Oblon, McClelland, Maier & Neustadt, L.L.P.

(57) ABSTRACT

A device for inspecting a surface of an electrically conductive part, the device having a plurality of eddy current probes arranged on a convex surface of the device together with an applicator for applying the probes against the surface to be inspected into which the device is inserted, wherein the probes are fastened on flexible strips extending beside one another in a longitudinal direction of the device, the applicator including a deformable material, that, on being compressed along the longitudinal direction, gives rise to expansion transversely to the longitudinal direction, the expansion deforming the strips so as to apply the probes against the surface.

12 Claims, 2 Drawing Sheets

(58) Field of Classification Search
CPC ......... G01N 27/904; G01N 2291/2636; G01N 2223/628; G01N 21/954; G01N 2021/9542; G01N 2021/9548; G01M 3/005; G01M 3/246

See application file for complete search history.

(56) References Cited

U.S. PATENT DOCUMENTS

| | | | |
|---|---|---|---|
| 4,506,219 A * | 3/1985 | Lee | E21B 17/1021 175/325.2 |
| 4,668,912 A | 5/1987 | Junker | |
| 4,889,679 A | 12/1989 | Snyder et al. | |
| 5,365,331 A * | 11/1994 | Tamburrino | G01M 3/005 356/241.6 |
| 5,465,045 A | 11/1995 | Derock | |
| 2002/0135363 A1 | 9/2002 | Trantow et al. | |
| 2003/0155914 A1 | 8/2003 | Tsukernik et al. | |
| 2004/0217759 A1 | 11/2004 | Burkhardt et al. | |
| 2005/0083050 A1 | 4/2005 | Tsukernik et al. | |
| 2007/0120559 A1 | 5/2007 | Plotnikov et al. | |
| 2010/0007342 A1 * | 1/2010 | Lepage | G01N 27/904 324/240 |
| 2013/0193953 A1 * | 8/2013 | Yarbro | E21B 47/082 324/76.77 |
| 2013/0319540 A1 * | 12/2013 | Hegner | F16L 55/16455 137/15.08 |
| 2016/0025682 A1 * | 1/2016 | Walker | G01N 27/9033 324/222 |

FOREIGN PATENT DOCUMENTS

| | | |
|---|---|---|
| JP | 5-119023 | 5/1993 |
| JP | 11-051906 | 2/1999 |
| JP | 2000-298117 | 10/2000 |
| JP | 2011-120800 | 6/2011 |

* cited by examiner

DEVICE FOR INSPECTING A SURFACE OF AN ELECTRICALLY CONDUCTIVE PART

TECHNICAL CONTEXT

The invention lies in the field of techniques for inspecting mechanical parts, in particular engine parts, for example parts of turbine engines, and in particular parts that include holes.

Numerous engine parts are critical, and if they rupture they are likely to have severe repercussions on the entire system, e.g. an aircraft.

The present invention relates particularly, but not exclusively, to parts in which a hole has been made. Such holes, which may be of various shapes, and in particular of elongate shapes with a middle axis, might include flaws, i.e. surface roughnesses that may act as starting points for rupture of the part.

Such flaws may appear while the hole is being machined, e.g. by using electrical discharge machining (EDM), or else while the part is in use, e.g. in an engine.

In numerous situations, it is necessary to inspect parts to ensure that there is no risk caused by the presence of such flaws. Such inspections may be performed on parts that are new or on parts that have already been used.

One known inspection technique is the eddy current method, consisting in verifying that the material is continuous by measuring currents that have been induced by a magnetic field.

Such a method is performed using a sophisticated measurement device generally having a plurality of eddy current probes or points. Such devices are known that are mounted on articulated metal arms with springs or brushes, which are fragile, thereby constituting a first problem.

Furthermore, the construction of such probe systems generally needs to be revised whenever attention is given to a hole of a shape that is different from the shape of the hole for which the system was initially designed, in order to take account of the curvature of the middle axis of the hole. Thus, the positioning and the length of the arms or the brushes need to be revised, which is complicated and expensive. Furthermore, it is very difficult to position such devices while using an automatic protocol, with a robot or with complex positioning tooling.

Finally, it is often necessary to change the probe in order to finish off observations both on a given hole and also on its opening or its end. Specifically, guiding a system of probes at the opening or at the end of a hole is particularly awkward, and it is preferred to use specific probes for those difficult zones.

Finally, existing systems are complex to implement, and excessively expensive because of the multiplicity of devices that need to be designed for holes that are different or even for only a single type of hole.

The invention seeks to resolve those difficulties.

DEFINITION OF THE INVENTION AND THE ASSOCIATED ADVANTAGES

To solve these difficulties, there is proposed a device for inspecting a surface of an electrically conductive part, in particular the inside surface of a hole, the device having a plurality of eddy current probes arranged on a convex surface of the device together with application means for applying the probes against the surface to be inspected into which the device is inserted, the device being characterized in that the probes are fastened on flexible strips extending beside one another in a longitudinal direction of the device, said application means comprising a deformable material that, on being compressed along said longitudinal direction, gives rise to expansion transversely to the longitudinal direction, said expansion deforming said strips so as to apply the probes against the surface.

By means of this device, a tool is made available that is much simpler to use, that is capable of adapting to numerous situations, and that is robust and inexpensive to fabricate and to use. The number of eddy current probes arranged on the tool may be large, insofar as there is no need to use a respective metal arm with a spring for each of them.

The probe may be handled by a robot, and measurement is entirely satisfactory, because of the way the probe adapts to the surfaces against which it is applied.

The surfaces in question are constituted in particular by the inside surfaces of holes, however the device can be used for inspecting other surfaces. In general manner, with this device there is no need to develop numerous probes for one or more particular applications, since the device can be adapted to most configurations. In particular, when inspecting the surfaces of holes, the device generally makes it possible to inspect not only the main surface of the hole, but also its end wall and its opening, thereby providing an improved field of observation. Finally, the time required for inspection is shortened.

Depending on the embodiment, the flexible strips are flexible printed circuits, which are advantageous since they are in expensive, or flexible metal strips. The deformable material may be silicone or any other deformable material.

In an advantageous embodiment, the deformable material is placed longitudinally between two compression parts, and the longitudinal compression of the deformable material is obtained by using a cable that is fastened to one of the two parts and that is slidable relative to the second part. In certain embodiments, it is proposed that the compression in the longitudinal direction is limited by an abutment.

Advantageously, said convex surface is a circular or elliptical circumference of the device. This makes it possible to inspect holes for which the circumference of the device is adapted.

In such a configuration, the device includes at least one additional set of flexible strips on a circumference of the device, the strips being compressed outwards from the device in order to guide the probe perpendicularly to the wall of the hole or to protect the eddy current probes on the device entering or leaving the hole. The device thus protects the eddy current probes so as to avoid them being damaged when the device is being inserted into or extracted from the hole that is to be inspected.

The device may include two such additional sets of flexible strips, referred to as "guides", one upstream from said plurality of eddy current probes and the other downstream from said plurality of eddy current probes. The flexible strips of the guide assembly preferably exert pressure on the walls that is greater than the pressure exerted by the flexible strips carrying the probes when they are applied against the walls.

The invention also provides a method of fabricating a device as described above, comprising forming slits in a flexible plate, so as to form flexible strips that are held together at their ends, so as to carry at least one probe per strip, and a step of molding the deformable material against the face of the flexible plate that is opposite from the eddy current probes. This fabrication method is particularly simple and practical to perform, and constitutes one of the contributions of the present invention.

The invention is described below with reference to the figures.

LIST OF FIGURES

DETAILED DESCRIPTION

Figure 1:
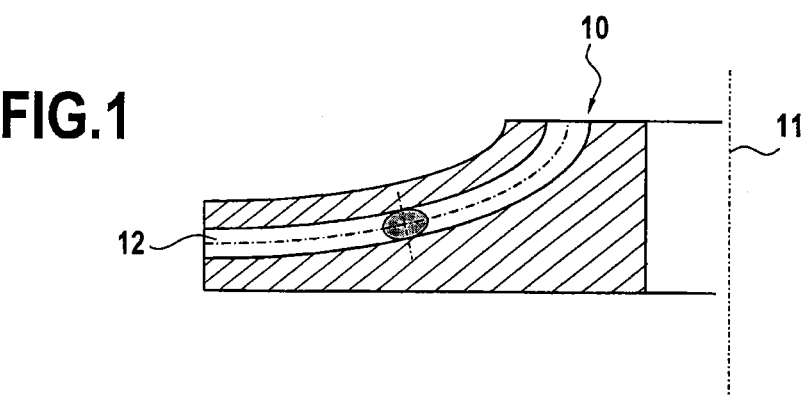
FIG. 1 shows a part including a hole that is to be inspected.

With reference to FIG. 1, there can be seen a part for inspection, specifically a disk 10, having an axis 11 on the right-hand side of the figure, and including an elongate hole 12 of elliptical section and of curvilinear axis. Until now, it has been necessary to use a plurality of eddy current probe tools for inspecting such a hole. Unfortunately, such tools are fragile and expensive, thereby making the operation difficult. Furthermore, the hole needs to be inspected in particularly careful manner since the part in question is extremely critical.

It should be observed at this point that the hole 12 has two openings, since both of its ends open out into faces of the part, however there are numerous situations in which it is likewise necessary to inspect holes having only one opening.

Figure 2:
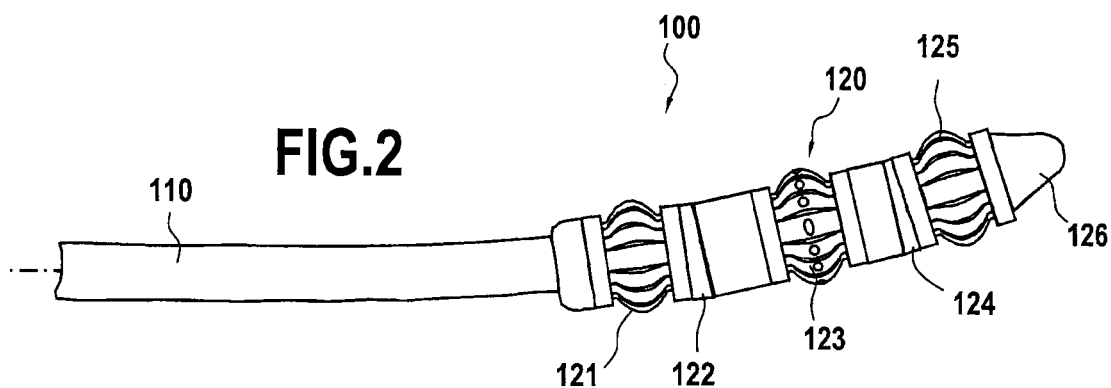
FIG. 2 shows an inspection device that has been developed to inspect the hole in the part of FIG. 1, in compliance with the principles of the invention.

FIG. 2 shows the inspection device 100 designed for searching for flaws in the hole 12. The device is of elongate shape, and it comprises a flexible drive sheath 110 having a head 120 fastened to one of its ends, which head is made up of a plurality of elements. More precisely, the head comprises, starting from the sheath 110 and going towards the free end of the device: a first assembly that is flexible in compression, referred to as a "guide" 121; a flexible connection 122; an adjustable assembly that is flexible in compression, constituting the functional core 123 of the inspection device; a second flexible connection 124; and a second assembly that is flexible in compression and referred to as a "guide" 125. A tip 126 in the form of a cone terminates the device. It should be understood that even though the guides 121 and 125 are advantageous, they are not absolutely essential for performing the invention.

Concerning the functional core, the concept governing the operation of the functional core is novel and, compared with prior devices, it makes it possible to increase the number of eddy current probes that can be applied against the surface for inspection, while also reducing the associated inspection time.

Figure 3:
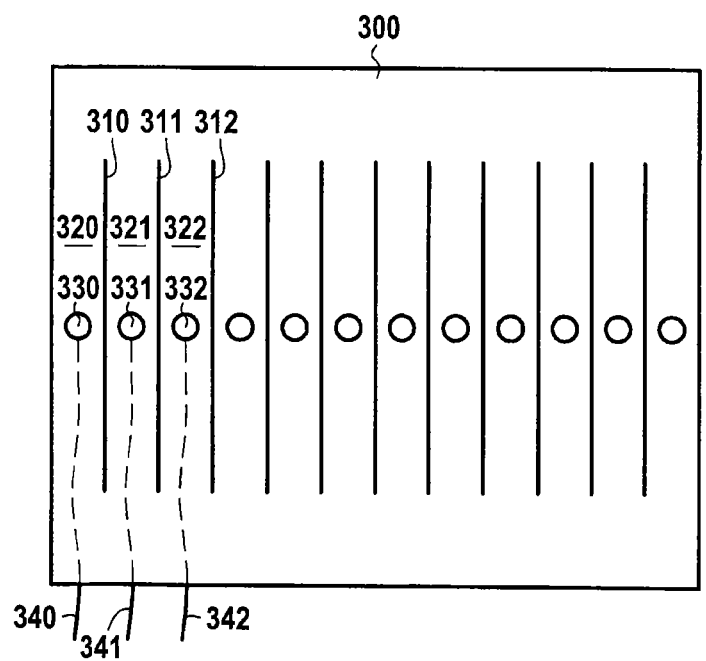
FIG. 3 shows a step in fabricating such an inspection device.

FIG. 3 shows a step in a process of fabricating an inspection device of the kind shown in FIG. 2. A flexible printed circuit plate 300 of rectangular shape is formed with through slits 310, 311, 312, . . . that are mutually parallel, and in this example parallel to the long dimension of the plate. By way of example, each slit extends lengthwise over the central two-thirds of the plate 300. The slits are spaced apart from one another equidistantly so as to define strips 320, 312, 322, . . . , that are held to one another by the non-slit material outside the central two-thirds of the plate 300. Between two adjacent slits, at equal distances from each of them, and halfway along them, eddy current probes 330, 331, 332 are put into place either before or after the slits are made. Each probe is provided with a respective electrical connection 340, 341, 342, . . . .

Figure 4:
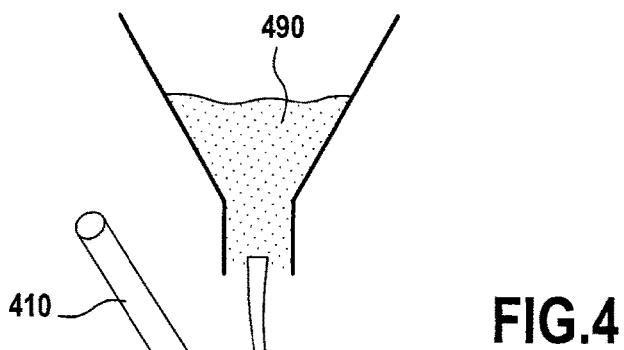
FIG. 4 shows a subsequent fabrication step.

FIG. 4 shows the subsequent step of fabricating the inspection device. The plate 300 is rolled into a cylinder 400 around an axis that is parallel to the slits, so that the probes face outwards, and so that deformable material 490 can be injected or cast into the inside of the cylinder through one of its two openings in order to match its shape by molding.

Prior to injecting or casting the deformable material 490, the electrical connections 340, 341, 342, . . . of the probes are arranged so as to exit the cylinder via its second opening. A pin 410 is placed in the center of the cylinder so as to reserve a cylindrical bore in the middle of the injected or cast material. An end wall 420 also serves to prevent the deformable material 490 escaping from the cylinder through the second opening. Finally, a banding tool 430 (or outer molding tool) surrounds the strips to prevent them from splaying axially while the deformable material 490 is being deposited. The tool preferably has the same shape as the hole to be inspected for which the probe is being fabricated, and it preferably has dimensions that are slightly smaller than those of the hole.

It should be understood that the cylinder shown in the figures is on a circular base, but that it is also possible to use a cylinder on a base that is elliptical or indeed of some other shape.

As mentioned at the end of this document, the plate 300 is not necessarily shaped to take the form of a closed cylinder, although the example shown relates to such a closed cylindrical shape, and in any event it becomes deformed to take on the shape of a convex cylinder, within which the molding is performed.

In a particular embodiment, the assembly of FIG. 4 is made by placing the plate of FIG. 3 on two supports (not shown) that define the upstream and downstream openings of the structure. A sheath or adhesive tape serves to hold the printed circuit on the support and to provide the necessary sealing at these openings. In certain embodiments, the pin 410 is used to align the two supports. In this embodiment, once the cylinder has been formed, it is inserted in two molding preforms, one being a central cylindrical axis (corresponding to the pin 410) and the other being an outer enclosure (corresponding to the banding tool 430). Both molding preforms are coated in unmolding substances, such as Teflon (registered trademark), which may be obtained by spraying or by being deposited in sheet form. Teflon sheets also make it possible to leave clearance between the outer enclosure and the printed circuit. A stopper (corresponding to the end wall 420), e.g. a silicone stopper, is put into place to obstruct one of the openings of the cylinder, through which the electrical connection wires for the probes are nevertheless extracted.

The deformable substance 490 is injected or cast in such a manner as to fill the volume of the cylinder 400, in part or in full.

Once the deformable material 490 has been injected or cast and once it has finished setting, the banding 430 and the pin 410 are removed. The banding has enabled the deformable substance 490 to take the shape of the cylinder 400 without deforming it, and the pin 410 has served to create a central cylindrical bore from one end of the device to the other, inside the deformable substance 490.

Figure 5:
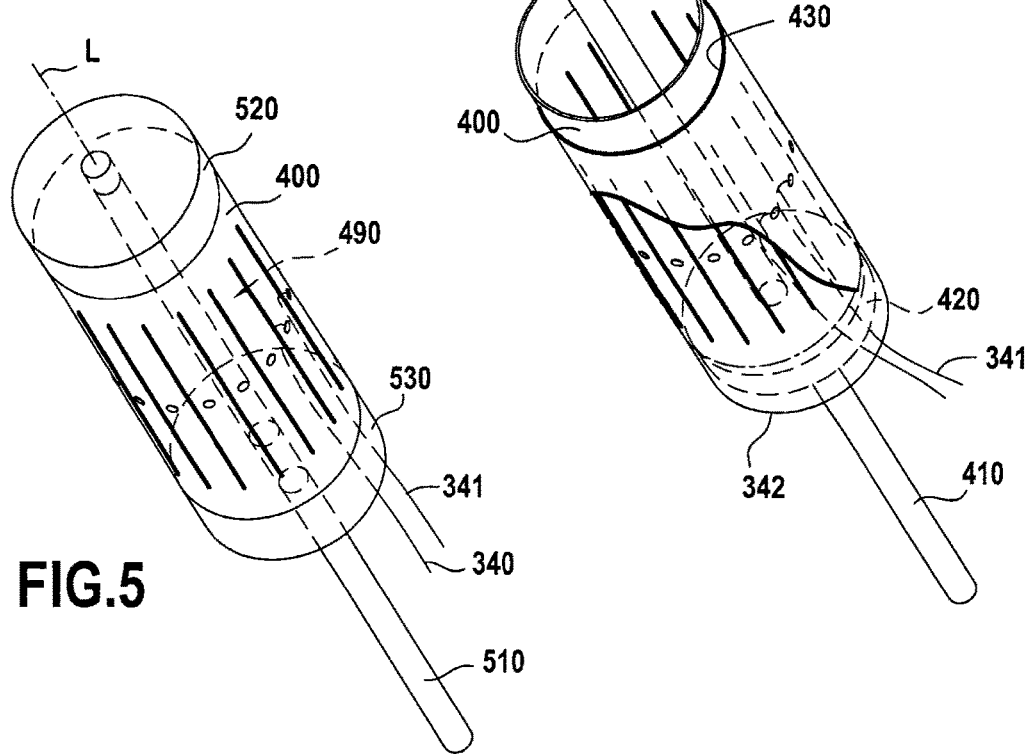
FIG. 5 shows a central assembly of the FIG. 2 inspection device, obtained after performing the steps shown in FIGS. 3 and 4.

FIG. 5 shows the device at a later step in its fabrication. A cable 510 has been inserted in the bore created that the center of the device and it is fastened via one end to a presser part 520 that is placed in one of the openings of the cylinder 400 so as to be in a position to press against the deformable substance 490 molded inside the cylinder 400. Where necessary, the presser part 520 is fastened to the cylinder 400, e.g. with an adhesive tape or with a sheath placed on the end of the cylinder. The cable 510 leaves the cylinder 400 via the other opening, either through or beside a retaining part 530 that also bears against the deformable substance 490 and that, where necessary, is fastened to the cylinder 400, e.g. using adhesive tape or a sheath placed on the end of the cylinder.

By way of example, the presser and retaining parts 520 and 530 may be the support used for holding the plate 300 in the form of the cylinder 400 prior to molding. Other solutions are possible, it being possible for these two parts to be inserted into the structure at various potential moments. The end wall 420 as shown in FIG. 4 is retained; however in certain embodiments, it could be removed, where necessary, once the deformable substance 490 has been molded.

The cable 510 may in particular be crimped onto the presser part 520. Furthermore, the cable 510 may have a stroke that is limited by an abutment formed by a pair constituted by a cable tube (not shown) and an abutment washer (not shown). In such an embodiment, the cable 510 is inserted in a tube that begins level with the presser part 520 and that terminates, when the cable is not being subjected to traction, at a given distance from the outlet of the retaining part 530. The cable 510 and the tube are secured to each other for movement in translation relative to the deformable substance 490 and the retaining part 530. The abutment washer surrounds the cable at its exit from the retaining part 530, allowing it to move, but preventing movement of the tube. Thus, when traction is applied to the cable 510, its stroke is blocked by the tube meeting the washer.

Figure 6:
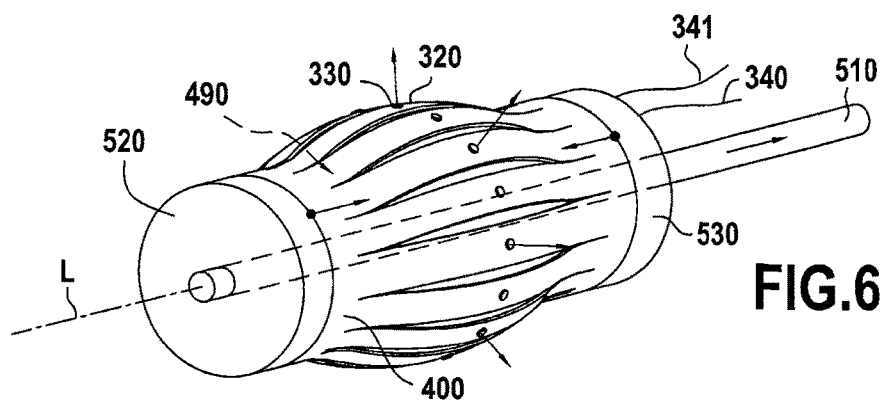
FIG. 6 shows the same assembly in operation.

As shown in FIG. 6, beside the retaining part 530, the cable 510 may be subjected to traction that acts by pulling on the presser part 520. Traction on the cable 510 then leads to longitudinal pressure (in the direction L) between the presser part 520 against the deformable substance 490 molded in the cylinder 400. The function of the retaining part 430 is to retain the deformable material, which is then being compressed longitudinally. This has the consequence of the deformable material bearing against the walls of the cylinder, enabling the strips 320, 321, 322, . . . to expand radially, the strips becoming curved and splaying apart from one another.

Preferably, since the retaining and presser parts 530 and 520 are arranged symmetrically relative to the eddy current probes 330, 331, 332, . . . , and relative to the mass of deformable substance 490 molded in the connect, the maximum expansion of the deformable substance takes place along the circumference of the cylinder that carries the probes 330, 331, 332, . . . , so that, when the device is in use, the probes are pressed against the wall of the hole that is to be inspected and into which the device has been inserted. The length of the stroke of the cable determines the maximum expansion that can be given, in use, to the circumference of the cylinder, and thus the pressure with which the eddy current probes 330, 331, 332, . . . , are applied. It is proposed to define this length by performing tests on the probe, as a function of the type of hole that is to be inspected.

It should be understood that other longitudinal compression systems could be used, for the purpose of causing the deformable substance 490 to expand in a plane perpendicular to the direction L.

Compression is controlled from a control station (not shown), by a human operator or by a robot.

Returning to the structure shown in FIG. 2, the guides 121 and 125 may be made in the same manner as the functional core 123, using the same principles as those shown in FIGS. 4 to 6, while naturally omitting the eddy current probes and their electrical connections. However for the guides 121 and 125, the compression of the flexible printed circuit may be defined in final manner on assembly, by securing the second end of the cable 510 or by setting the compression with means other than a cable. The compression could also be adjusted when making the hole that is to be inspected, in order to take account of the exact dimensions of the hole.

This is different from that which is done with the functional core 123, where the cable 510 enables the degree of compression to be controlled from a control station, after the device has been inserted inside the hole for inspection. On this topic, it should be understood that the cable 510 of the functional core 123 and the electrical connections 340, 341, 342, . . . are taken to a control station inside the flexible drive sheath 110.

The invention is not limited to the embodiments described, but extends to any variant coming within the ambit of the scope of the claims.

In particular, it is not necessary to place the eddy current probes around a closed circumference of the device, in particular in the event where the surface that is to be inspected does not constitute a closed section of a hole.

It is thus possible to use the principles of the invention while shaping the plate 300 into a cylinder having a base that is a semicircle or half an ellipse, thereby constituting a surface that is convex, with its shape being closed by an extra part, which may for example be plane, and which is preferably not deformable. The deformable substance (silicone) is then molded in a cavity formed by the plate 300 and the extra part. Thus, the effect of deforming the strips takes place only over a semicircle or half an ellipse.

Independently of the above comments, it should also be understood that in order to implement the invention it is not essential for the probes to be equidistant, nor even for them to be uniformly distributed over the convex surface, nor is it essential for all of the strips to be of the same width.

The invention claimed is:

1. A device for inspecting a surface of an electrically conductive part, the device comprising:
   a plurality of eddy current probes arranged on a convex surface of the device; and
   an applicator for applying the probes against the surface to be inspected into which the device is inserted,
   wherein the probes are fastened on flexible strips extending beside one another in a longitudinal direction of the device so as to define a flexible hollow cylinder,
   wherein said applicator includes:
      a deformable material distinct from said flexible strips and mounted inside said hollow cylinder,
      a retaining part abutting a first end of the deformable material, and
      a presser part abutting a second end of the deformable material, the presser part being is movable relative to the retaining part in the longitudinal direction, and
   wherein when the presser part moves towards the retaining part, said deformable material is compressed along said longitudinal direction and expands transversely to the longitudinal direction such that the deformable material deforms and said strips apply the probes against the surface.

2. The device according to claim 1, wherein the flexible strips are flexible printed circuits.

3. The device according to claim 1, wherein the flexible strips are flexible metal strips.

4. The device according to claim 1, wherein the deformable material is silicone.

5. The device according to claim 1, wherein a cable is fastened to the presser part for moving the presser part.

6. The device according to claim 1, wherein the compression in the longitudinal direction is limited by an abutment.

7. The device according to claim 1, wherein said convex surface is a circumference of the device.

8. The device according to claim 7, wherein the device further includes at least one additional set of flexible strips on a circumference of the device, the at least one addition set of flexible strips being compressed outwards from the device so as to present a guide assembly which guides the probes perpendicularly to a wall of a hole or to protect the eddy current probes on the device entering or leaving the hole.

9. The device according to claim 8, further comprising two such additional sets of flexible strips, one upstream from said plurality of eddy current probes and the other downstream from said plurality of eddy current probes.

10. The device according to claim 8, wherein the flexible strips of the guide assembly exert pressure on the walls that is greater than the pressure exerted by the flexible strips carrying the probes when flexible strips of the guide assembly are applied against the walls.

11. A method of fabricating a device according to claim 1, comprising:

forming slits in a flexible plate, so as to form the flexible strips that are held together at ends thereof, so as to carry at least one eddy current probe per strip; and molding the deformable material against a face of the flexible plate that is opposite from the eddy current probes.

12. The device according to claim 1, where the retaining part and the presser part are circular.

* * * * *